United States Patent [19]
Brown

[11] Patent Number: 5,148,701
[45] Date of Patent: Sep. 22, 1992

[54] DOMESTIC WATER TESTER

[75] Inventor: John J. Brown, Pullman, Wash.

[73] Assignee: Washington State University Research Foundation, Pullman, Wash.

[21] Appl. No.: 698,730

[22] Filed: May 10, 1991

[51] Int. Cl.[5] ............................................. G01N 33/18
[52] U.S. Cl. ....................................... 73/61.41; 4/314
[58] Field of Search ............... 73/61.1 R, 40.7; 4/314, 4/266; 116/200, DIG. 1, DIG.7

[56] References Cited

U.S. PATENT DOCUMENTS

| | | | |
|---|---|---|---|
| 3,469,453 | 9/1969 | Nelson | 73/863.02 |
| 3,841,484 | 10/1974 | Domnick | 210/95 |
| 3,966,439 | 6/1976 | Vennos | 55/270 |
| 4,198,301 | 4/1980 | Iwatani | 210/274 |
| 4,359,907 | 11/1982 | Morin et al. | 73/863.21 |
| 4,770,028 | 9/1988 | Flippo, Jr. | 73/40.7 |
| 4,873,727 | 10/1989 | Homan | 4/226 |
| 4,890,485 | 1/1990 | Hsu | 73/61.1 R |
| 4,919,892 | 4/1990 | Plumb | 73/61.1 R X |
| 4,935,726 | 6/1990 | Buro et al. | 73/61.1 R X |

Primary Examiner—Hezron E. Williams
Assistant Examiner—Joseph W. Roskos
Attorney, Agent, or Firm—Wells, St. John, Roberts, Gregory & Matkin

[57] ABSTRACT

Water testing apparatuses and methods for detecting contaminants in water supplies, such as from wells or other domestic water sources. The apparatuses are for use in reservoirs, such as a water closet of a sanitary toilet. They include an enclosure which defines an interior chamber which is intermittently charged with water. The water charged to the interior chamber is passed through one or more filters, preferably a packed column, which removes or otherwise indicates the presence of contaminants in the water. A counter measures the water passed through the system. Water is discharged from the interior chamber using a siphon. The siphon and restriction of flow caused by the filters help control the direction of flow and substantially prevent backflow. The summit of the siphon includes a relief valve for venting gas during filling of the siphon discharge.

23 Claims, 3 Drawing Sheets

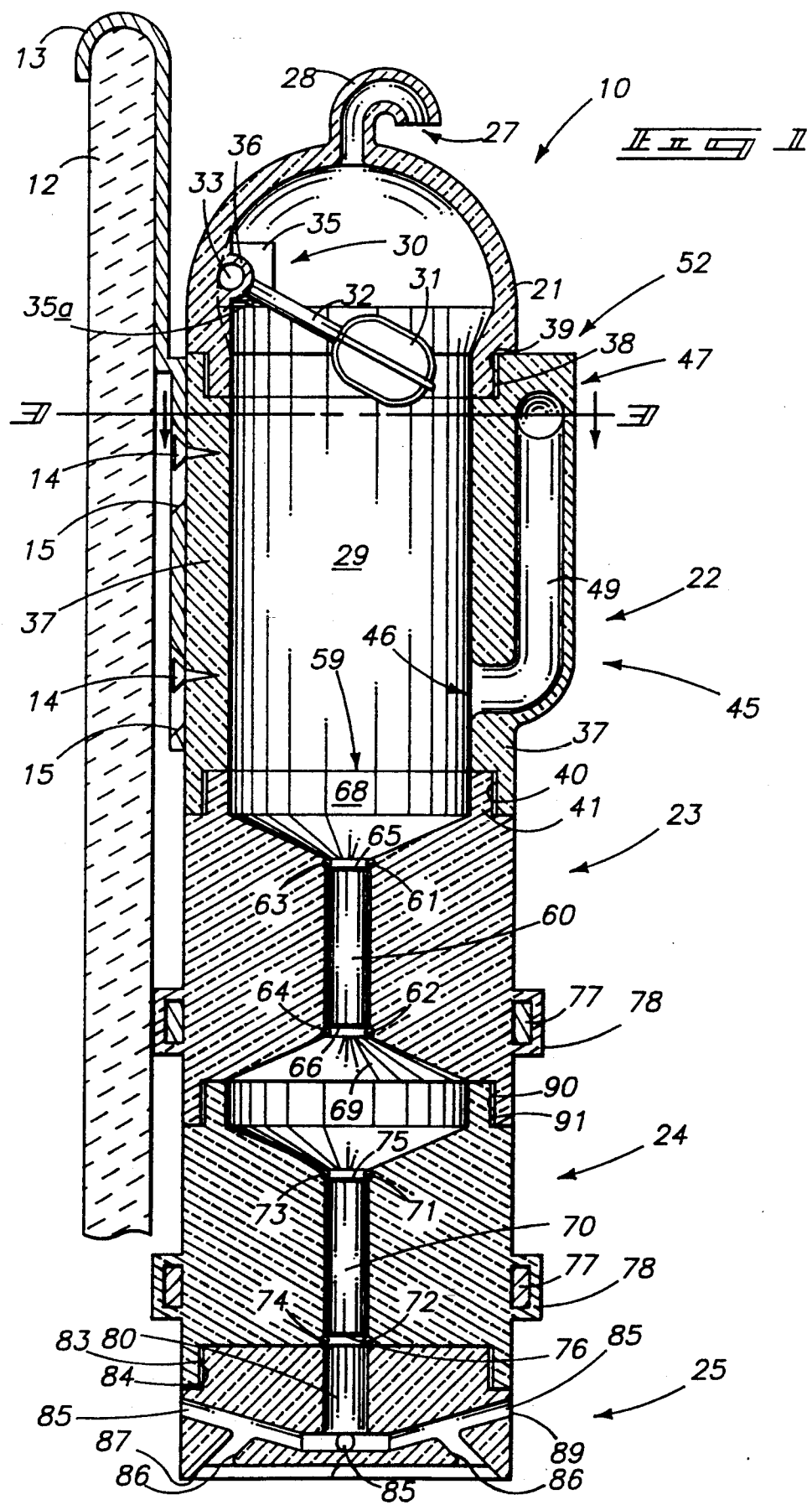

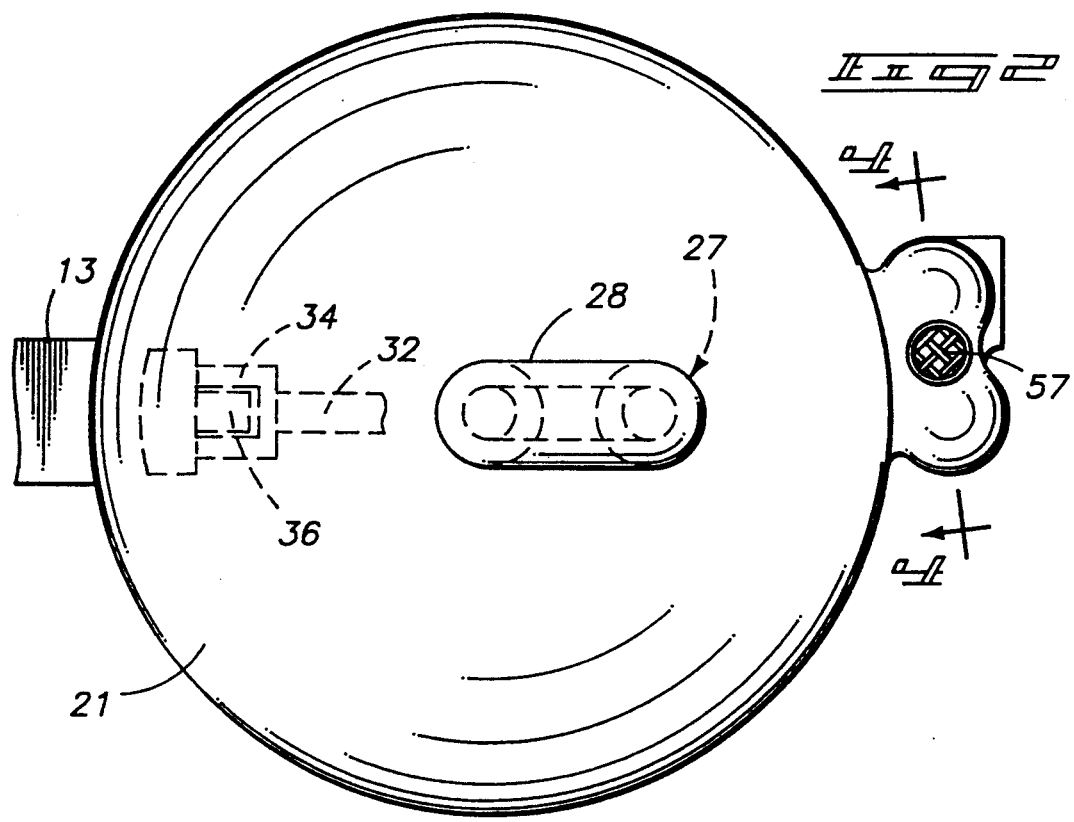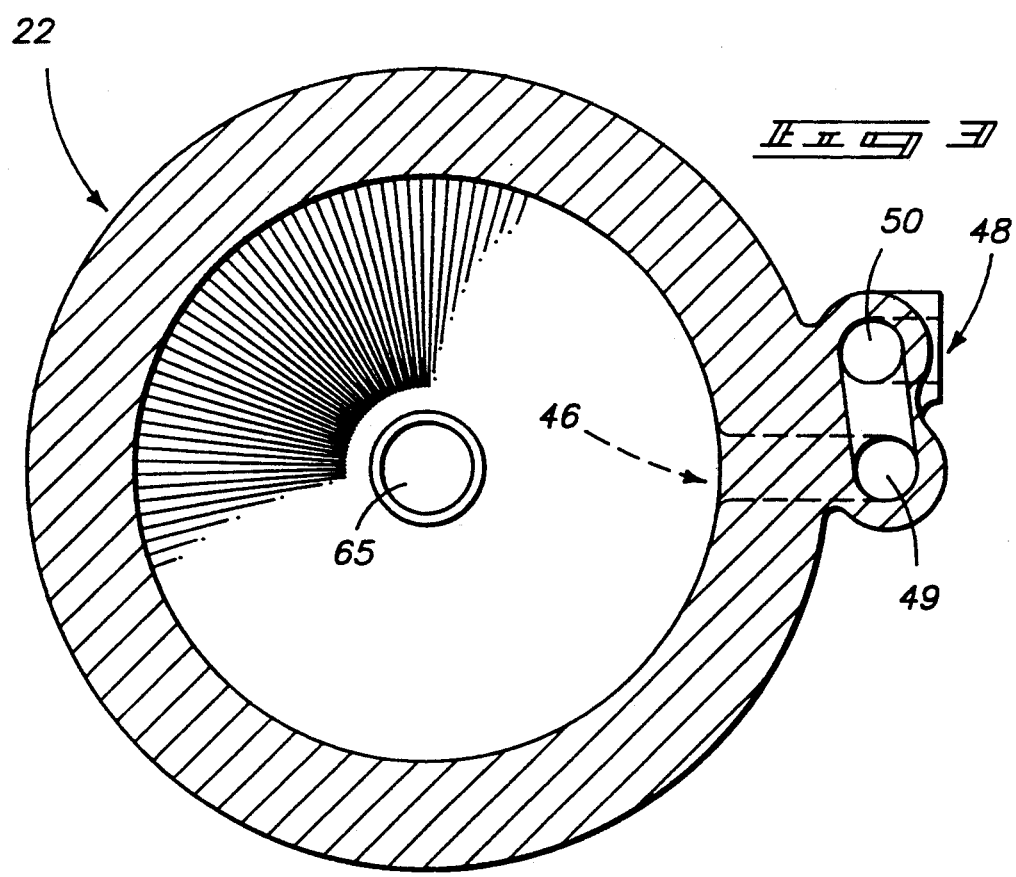

DOMESTIC WATER TESTER

TECHNICAL FIELD

The technical field of this invention is systems and methods for testing contaminant levels in domestic water supplies using apparatuses which are mounted within reservoirs having a fluctuating water level, such as in water closets of sanitary toilets.

BACKGROUND OF THE INVENTION

There is increasing concern about deteriorating quality of domestic water supplies. In order to determine water quality, more and more testing is being conducted to determine the presence of pesticides, nitrates, microorganisms, metals, hydrocarbons, and other contaminants which are undesirable as constituents of domestic water supplies.

Testing is most difficult in small scale water supplies, such as private farm and residence wells, because of the trouble and cost of taking samples and transporting them to laboratories for analysis. The testing of such water systems is also rendered less accurate by this approach because the samples are relatively small quantities taken at a specific time or times and therefore do not necessarily include contaminants which may appear intermittently or periodically. For example, spring runoff may flush pesticides and nitrates from farm land toward lowland areas where wells are often located. This may cause an increase in pesticide and nitrate levels in domestic water supplies dependent on various factors, such as the depth of the aquifer, casing of well shaft, and the permeability of the overlying soil. Because of these and other factors, testing may be conducted at a time of the year demonstrating reduced levels or increased levels of contaminants. This reduces the reliability of such testing.

Where testing is done at specific times and the contamination problem is intermittent rather than seasonally periodic, then the reliability problem is even more significant. An intermittent contamination problem may pose significant short term exposures without necessarily leaving sufficient residue for accurate detection at later times.

Laboratory testing of domestic water supplies also has associated costs which reduce the frequency with which laboratory analyses can be run to determine the presence of contaminants. In large scale water systems frequent testing must be conducted and the arrangements for doing so can be efficiently arranged and the cost spread over thousands of consumers. With private or small scale water systems testing on a repeated basis can only be justified on a cost basis if there is a problem or suspected problem of significant concern. This increases the risk that millions of private water systems are not being adequately tested to provide satisfactory monitoring of water quality. In reality almost all small scale water systems are not monitored in any significant way unless a problem has been perceived or is suspected.

If contaminants are heavy metals, low level radioactive particles, or organics of low to medium toxicity, such contaminants may be present for long periods of time before noticeable effects occur. The noticeable effects may be serious and irreversible with long term poisoning or cancer as potential resulting effects. These health concerns have increased the need for the efficient and accurate testing of domestic water supplies.

Thus there has been a need in the art for more acceptable water quality testing. Particularly there has been a need for water quality testing systems which will provide effective medium to long term monitoring of water quality at low cost for small domestic water systems and wells. The novel systems described herein provide a significant step in the art of monitoring of such water supplies.

BRIEF DESCRIPTION OF THE DRAWINGS

Preferred embodiments of the invention are illustrated in the accompanying drawings, which are briefly described below.

FIG. 1 is a longitudinal sectional view of a preferred form of water quality testing apparatus according to this invention.

FIG. 2 is a top view of the testing apparatus of FIG. 1.

FIG. 3 is an enlarged cross-sectional view of the testing apparatus of FIG. 1 taken along section 3—3 of FIG. 1.

DETAILED DESCRIPTION OF THE PREFERRED EMBODIMENTS

Figure 5:
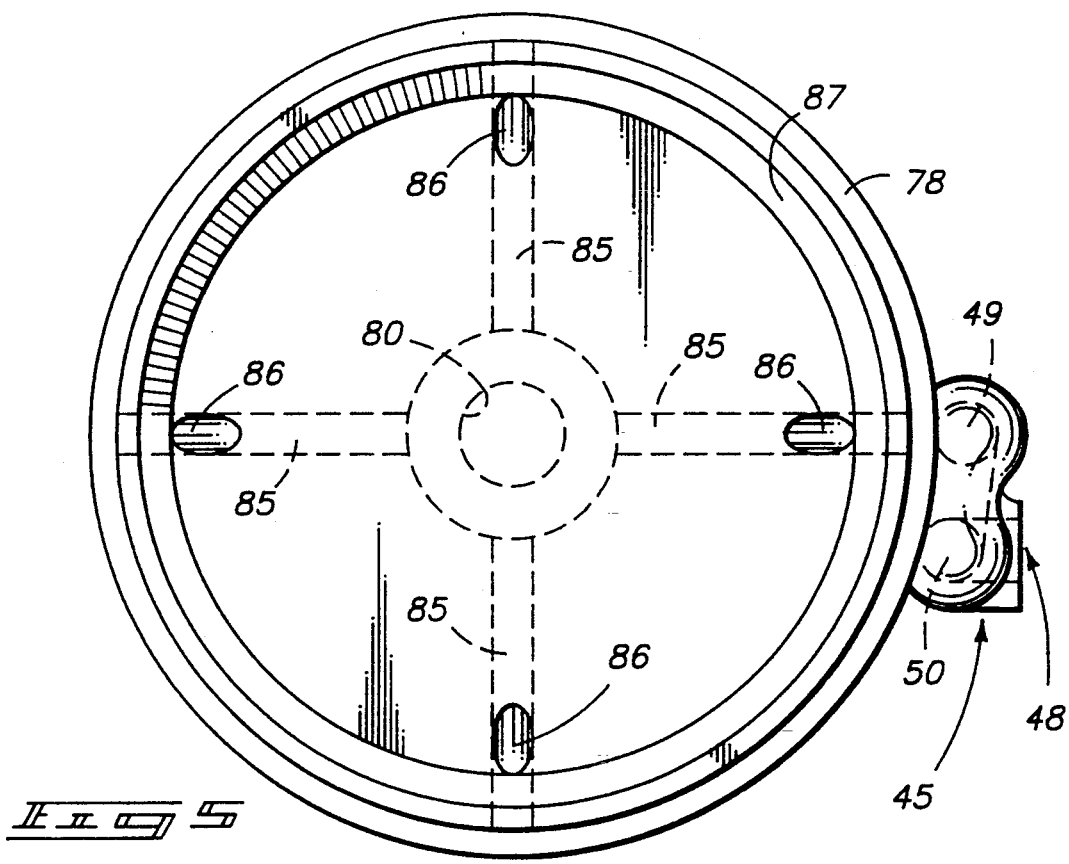
FIG. 5 is a bottom view of the testing apparatus of FIG. 1.

This invention disclosure is submitted in furtherance of the constitutional purposes of the Patent Laws "to promote the progress of science and useful arts" (Article 1, Section 8).

FIG. 1 shows a preferred domestic water testing apparatus 10 built in accordance with this invention. Testing apparatus 10 is shown mounted within the reservoir of a water closet 12 using a hanger bracket 13. Bracket 13 is connected to the testing apparatus in a suitable manner, such as by fasteners 14 which extend into a sidewall of the testing apparatus. The bracket can be provided with elongated beveled slots 15 which allow the position of the bracket relative to the remaining portions of the testing apparatus to be adjusted. This construction or other functional equivalent allows adjustment of the vertical position of the testing apparatus within the water closet or other reservoir to provide the desired water level within the testing apparatus.

Testing apparatus 10 is advantageously formed as an assembly of several parts. A first part or top piece 21 is joined to a second part or main body piece 22. Third and fourth parts 23 and 24 are water quality indicating pieces preferably in the form of filter holders. A fifth part 25 serves as a bottom end piece and intake for the testing apparatus. The assembly formed of parts 21-25 is advantageously shown connected using threaded connections for ease of assembly and disassembly. Suitable press fit connections, bayonet connections or other substantially fluid tight connections may alternatively be appropriate.

Top piece 21 is provided with a domed top which can be hemispherical, as shown. The upper portion of top piece 21 is provided with a vent 27 which allows gas to escape as water rises within the interior chamber 29. Vent 27 is advantageously provided with an inverted U-tube vent fitting 28. The U-tube vent construction greatly reduces the chance that water from the water closet may flow into the interior chamber of the testing apparatus without passing through the intake system and filters described in greater detail below.

Top piece 21 is also provided with a flow measuring counter 30. Counter 30 detects water within the interior chamber which has risen to a predetermined water charge level. As shown, counter 30 detects water within the interior chamber using a float 31 mounted on a float arm 32. Float arm 32 is provided with a clevis end piece 34 (FIG. 2) which is pivotally connected using pivot pin 33 to a pivot mount 36 formed along the interior of the wall of the top piece. A counter mechanism 35 is mounted to the wall of the top piece adjacent to the pivot mount in a position which provides mechanical interaction between the pivotally mounted float assembly and a trip 35a on the counter mechanism. Actuation of the counter trip causes the counter to record an indication that another charge of water has been provided in the interior chamber 29. Alternative flow counters which provide an indication of the total flow of water passing through the filters are also possible.

Top piece 21 is also provided with male threads 38 on a connection extension portion. Threads 38 are received within female threads 39 formed in the top receptacle of the main body piece 22.

Main body piece 22 has a cylindrical side wall 37 and is open along upper and lower ends to form a generally tubular structure. The main body piece has an interior space which forms the largest part of interior chamber 29. The interior of body piece 22 adjoins with interior spaces within the top part 21 and the third part 23 through the open upper and lower ends, respectively. The lower end of body piece 22 is advantageously provided with female threads 40 which receive male threads 41 formed on third part 23.

Main body piece 22 is also preferably adapted to form a discharge 45 serving to remove fluid from the interior of chamber 29. Discharge 45 has a chamber port 46 opening the interior wall of the main body piece toward the interior chamber 29. The discharge extends upwardly along a siphon uptake 49 to a siphon summit 47. From the siphon summit the discharge continues downwardly along a siphon downpipe 50 to an exterior discharge port 48 (FIG. 3).

Figure 4:
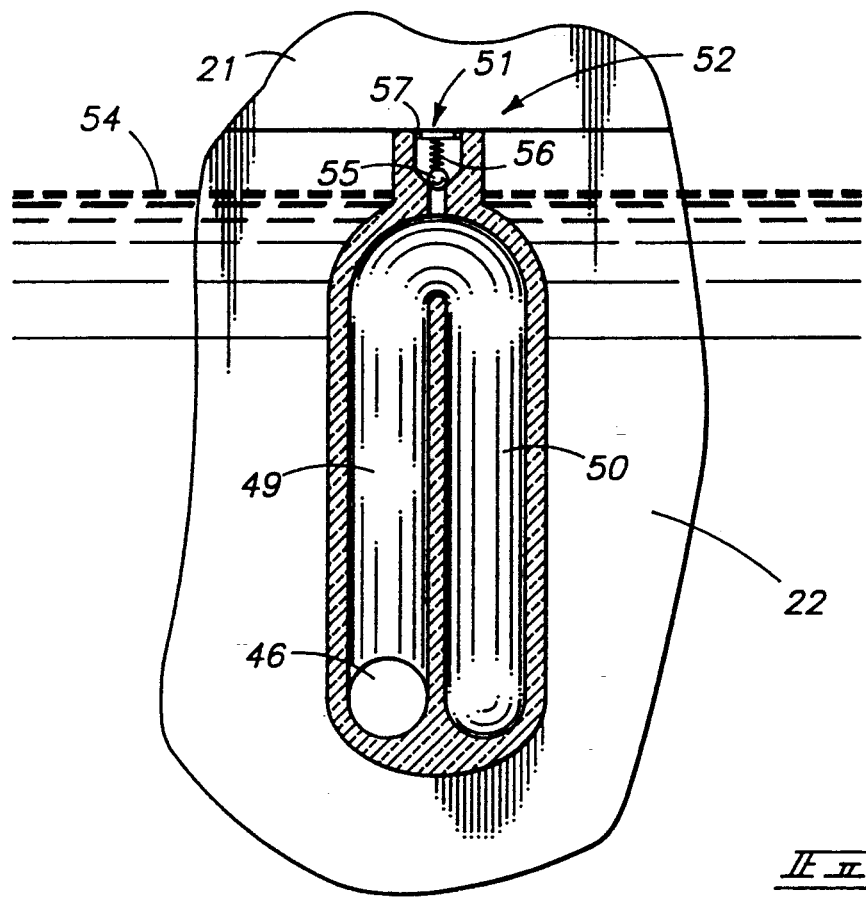
FIG. 4 is an enlarged cross-sectional view of the testing apparatus of FIG. 1 taken along section 4—4 of FIG. 2.

The siphon summit is provided with a siphon vent 51 which allows gas to escape as water flows upwardly in both the uptake 49 and downpipe 50 during filling of the testing apparatus and surrounding reservoir 12. The downpipe is filled with water from the water closet which passes inward through exterior discharge port 48. Water flows upward in uptake 49 as interior chamber 29 fills with water flowing in through intake 25 and filter holding pieces 23 and 24. The siphon summit vent is provided with a relief valve 52 which closes the vent after gas has been forced out and in preparation for siphoning. The water in the water closet and interior chamber is preferably brought to the fill mark represented by water level 54 as shown in FIG. 4. Relief valve 52 includes a valve piece 55 which is advantageously in the form of a small plastic ball. The valve piece seals against a valve seat formed in the vent. The valve piece is biased downwardly by its own weight into the sealing position and held there during siphoning by the vacuum pressures developed in the siphon. If needed, a small relief valve biasing spring 56 can optionally be provided to help locate and assure a very small downward force to bias the valve closed to maintain the desired pressure within the siphon during siphoning operation. A vent retainer 57 is provided at the upper opening of the vent to retain the ball shaped valve piece 55 and any spring 56 in proper position. Retainer 57 can advantageously snap fit into position within the vent receptacle which receives and forms part of relief valve 52.

Third part 23 is formed with a longitudinal passage 59 therethrough. The longitudinal passage includes an indicator compartment 60 which is adapted to hold a packed column of indicating material, such as those described hereinafter. The upper and lower ends of the indicator compartment 60 are provided with O-ring receiving grooves 61 and 62 which receive O-rings 63 and 64. O-rings 63 and 64 serve to hold thin membranes of porous material 65 and 66 which act as retainers to maintain particulate or bead shaped filtration or other indicating material within compartment 60.

At the upper end of longitudinal passage 59 is an upwardly facing funnel-shaped section 68 which forms the lower end of the interior chamber 29. The opposite, lower end of the longitudinal passage 59 is similarly provided with a funnel-shaped section 69 which is downwardly facing. The funnel-shaped section 68 includes a cylindrical portion and frustoconical portion. Funnel section 69 is frustoconical. The third and fourth parts 23 and 24 are joined by threads 90 and 91.

Fourth part 24 is constructed similar to third part 23 except the funnel-shaped section at the lower end has been eliminated to provide direct meeting between the indicator compartment 70 and the cylindrical intake collection passageway 80 formed in intake piece 25. The fourth part 24 includes O-ring grooves 71 and 72 for receiving O-rings 73 and 74 which act to hold porous retaining membranes 75 and 76 in the same fashion as for third part 23.

The third and fourth parts 23 and 24 are both advantageously provided with ballast means for counteracting buoyant forces developed as a result of water filling into water closet 12 faster than water can fill into interior chamber 29. The ballast is preferably provided in the form of annular ballast rings 77 mounted in suitable fashion to these parts. The ballast rings may advantageously be made of lead, in which case the ballast rings must be encapsulated to prevent undesired contamination of the water and erroneous results when the testing is for heavy metals, such as lead. As shown ballast rings 77 are encapsulated by encapsulation rings 78 integrally connected to the sides of parts 23 and 24.

The contaminant-indicating filter holding parts 23 and 24 are constructed in a modular manner with the upper ends provided with male threads of a desired size and lower ends provided with female threads for receiving the same size and type of threads. This allows any number of indicating sections to be assembled together in a serial arrangement for filtering or otherwise passing water and indicating the presence of contaminants in the water which passes therethrough.

The filtrating or other indicating materials preferred for use in testing apparatus 10 include a variety of particulate and bead materials which either chemically react with the contaminants, filter the contaminants from the water, or both. Examples of suitable materials include Bio-Beads ® SM-2 or SM-4 polystyrene-divinylbenzene adsorbents, or Amberlite ® XAD resin, both useful for absorbing or adsorbing pesticide contaminants. For heavy metals, the indicating materials are preferably ion exchange resins, such as AG ® brand 501-X8(D), 1-X8(OH—), and 50W-X8(H+). For nitrates, an AG ® 50W-X12 resin will be used. For microbial contaminants or small molecular weight contaminates, the indicating materials are preferably polyacrylamide gels, agarose gels, and specially prepared affinity gels having specific antibodies against the contaminants being detected which are ligated to a supporting gel, such as the polyacrylamide or agarose gels. A variety of other filtration or other biological chemical indicating chromatography media can alternatively be used.

Bottom end piece 25 is provided with a male threaded 83 portion which is received within a female threaded portion 84 in the lower end of fourth part 24. Bottom end piece 25 is provided with suitable passages to perform the intake functions which it serves. As shown, the intake is formed by a plurality of passages which connect with the intake collection passageway 80. The intake passages include upwardly sloping passageways 85. Passageways 85 slope upwardly from the intake collection passageway 80 toward the upper intake ports 89. Ports 89 serve as gas or bubble escape ports which allow bubbles to exit. Passageways 85 and ports 89 are advantageously four in number and at equiangularly spaced orientations of 90° about the central collection passageway 80. Passageways 85 slope upwardly to expel bubbles and gases coalescing from the water from the central intake passageway 80, 70, 60. The bubbles are expelled and do not create gas pockets adjacent to or within the filter compartments 60 and 70.

The intake also includes downwardly directed branch passages 86. Passages 86 branch from each of passageways 85 and extend downwardly to provide fluid communication with the bottom end of the intake piece 25. The bottom of piece 25 is advantageously provided with a bottom recess 87.

The novel operational methods of this invention will now be described in the context of describing the operation of testing apparatus 10. The testing apparatus 10 is utilized by installing it within a water closet of a toilet or other water reservoir which experiences a fluctuating water level caused by the inflow and outflow of a circulating supply of water. The unit is installed so that the high water level is at or above the summit 47 of the siphon. This assures that the siphon is filled with water when the reservoir is filled so that the siphon discharge from interior chamber 29 will operate properly. Water levels above the siphon summit 47 are also operable. Levels higher than vent 27 should be avoided to reduce the risk of significant water flows occurring into the interior chamber through that vent.

The methods also include passing water from the water closet 12 or other reservoir into the interior chamber 29. Water is passed from the water closet to the interior chamber in response to the rising level of water in the water closet. Such passing include intaking water into the intake ports formed by side intake ports 89 and the bottom intake port formed by bottom recess 87 and conjoining passages 86. The water passing through the intakes is convened in the central collection passageway 80 and conveyed upwardly by hydraulic pressure due to the relatively lower liquid level inside chamber 29 as compared to the level in the water closet 54. The filling of chamber 29 with water also involves venting the displaced gas, such as through vent 27, to prevent pressure buildup within the interior chamber.

The novel methods are also characterized by passing the inflowing water from the intake through at least one contaminant indicator for detecting the presence of at least one contaminant in water passed to the interior chamber. The passing of water through the contaminant indicator is preferably performed by filtering the water through one or more filtration passageways which contain appropriate filtration material which act as indication material indicating the presence of contaminants. The indication materials can operate by either filtering the contaminants from the water or by reacting or other wise indicating the presence of these materials in the water passing through the indicating material passageways or compartments 60 and 70.

The methods still further include measuring the flow of water passing through said at least one contaminant indicator. Said measuring is preferably accomplished by counting the charges of water which reach a predetermined chamber charging level within the interior chamber 29. The predetermined chamber charging level is advantageously measured by detecting the water level. The level can be detected by sensing such level using a interior chamber level sensing detector, such as by actuating float 31 and mechanically connected counter 35.

The methods of this invention additionally include discharging from the interior chamber water which has passed through the indicating material. This is preferably accomplished by siphoning water from the interior chamber when the fluctuating water level drops within the reservoir. The siphoning discharge occurs automatically as the reservoir water level drops. This occurs because the siphon tube discharge has been fully filled with water. To assure proper siphon discharge of water from the interior chamber, the methods further advantageously include venting of gas from the siphon discharge 45. This venting of gas occurs during filling of the reservoir and the passing of water from the reservoir to the interior chamber through the indicating material components and associated flow passages. The venting is also automatically controlled by relief valve 52 to thereby restrict venting during the siphoning to maintain the siphon vacuum within the discharge. The siphoning discharge removes water from interior chamber 29 down to a level approximately the same as the upper level of the interior discharge port 46.

After water has been discharged from the interior chamber, the testing apparatus substantially prevents backflow of water through parts 23-25 because of the restriction to water flow provided by the filters contained within filtration compartments 60 and 70 and retaining membranes 65, 66, 75 and 76. The siphon discharge 45 and the restrictive intersticial pore size of the flow passages through compartments 60 and 70 provide a flow direction control means which provides flow in one direction through the indicators. The elevated position of discharge interior port 46 provides a residual water level which maintains the compartments of parts 23-25 wetted during the period the reservoir 12 refills with water. This prevents bubbles from developing in the central inflow passageway defined by parts 23-25. The relatively quick refill time for typical sanitary toilet water closets is sufficient to maintain a substantially unidirectional flow through the compartments 60 and 70 to help assure the accuracy of the indicating materials for the corresponding water charges indicated by counter 35.

The indicating materials held in chambers 60 and 70 of either parts 23 or 24 can advantageously be provided with various dyes which are included in an ion exchange resin. The dye changes color in response to ions trapped therein and the resulting resin saturation. As the color changes to a significant degree the transparent sidewall of parts 23 or 24 allow the user to see that the testing apparatus is ready for analysis. The unit is then removed from the water closet and returned to a laboratory for analytical work to determine the extent of ions trapped and the levels of nitrates and other materials filtered or otherwise indicated by parts 23 or 24 from the water flow during the test period. The counter is read to indicate the volume of water which passed through the unit during the test. The concentrations of the contaminants are then calculated based upon the tested amounts and the volume of water passed to extract or otherwise indicate such levels of contamination.

In compliance with the statute, the invention has been described in language more or less specific as to structural features. It is to be understood, however, that the invention is not limited to the specific features shown, since the means and construction herein disclosed comprise a preferred form of putting the invention into effect. The invention is, therefore, claimed in any of its forms or modifications within the proper scope of the appended claims appropriately interpreted in accordance with the doctrine of equivalents.

I claim:

1. A water testing system for mounting within a reservoir which experiences a fluctuating water level, such as the water closet of a sanitary toilet, comprising:
    an enclosure defining an interior chamber having a chamber volume for receiving intermittent charges of water thereinto;
    at least one intake through which water held within the reservoir about external portions of the enclosure flows toward the interior chamber;
    at least one indicator holder; said at least one indicator holder having means for holding at least one contamination indicator within a flow of water passing through the interior chamber;
    at least one discharge connected in fluid communication with the interior chamber which allows controlled discharge of water when the water level drops within the reservoir about external portions of the enclosure;
    a flow counter for indicating the flow of water through said at least one indicator holder;
    flow direction control means for controlling flow of water through said at least one indicator holder to substantially one direction.

2. A water testing system according to claim 1 and further comprising indicator material held within said at least one indicator holder.

3. A water testing system according to claim 1 wherein said flow direction control means includes a siphon.

4. A water testing system according to claim 1 wherein said flow direction control means includes a siphon in said at least one discharge.

5. A water testing system according to claim 4 and further comprising a siphon relief valve for allowing gas to escape from a summit of the siphon.

6. A water testing system according to claim 1 wherein said flow direction control means includes a siphon in said at least one discharge, and indicator material having small interstitial pore size creating impediment to backflow of water from the interior chamber toward said at least one intake.

7. A water testing system according to claim 1 wherein said at least one intake is below the interior chamber during use and said flow direction control means includes a siphon in said at least one discharge.

8. A water testing system according to claim 1 wherein said at least one intake is below the interior chamber during use, said at least one indicator holder is between said interior chamber and said at least one intake, and said flow direction control means includes a siphon in said at least one discharge.

9. A water testing system according to claim 1 wherein said at least one intake is below the interior chamber during use, and said at least one indicator holder is between said interior chamber and said at least one intake.

10. A water testing system according to claim 1 wherein said at least one indicator holder is connected to other portions of the water testing system in a modular arrangement to allow variable number of indicator holders to be assembled together.

11. A water testing system according to claim 1 wherein said at least one indicator holder is connected to other portions of the water testing system in a modular arrangement to allow variable number of indicator holders to be assembled together in a serial arrangement.

12. A water testing system according to claim 1 wherein said at least one indicator holder is connected to other portions of the water testing system in a modular arrangement to allow variable number of indicator holders to be assembled together between said interior chamber and said at least one intake.

13. A water testing system according to claim 1 and further comprising ballast means.

14. A water testing system according to claim 1 and further comprising at least one hanger for hanging the water testing system.

15. A water testing system according to claim 1 and further comprising:
    at least one hanger for hanging the water testing system;
    ballast means.

16. A water testing system according to claim 1 wherein said flow counter includes a level detecting means for detecting the level of charges of water supplied to the interior chamber.

17. A water testing system according to claim 1 wherein said flow counter includes a float which moves in response to charging of water to and discharging from said interior chamber.

18. A water testing system according to claim 1 and further comprising at least one vent means for venting the interior chamber to allow filling of the interior chamber with charges of water.

19. A method for testing water using a water reservoir which contains a body of water which experiences fluctuating water level due to the fluctuating flow of water therethrough, comprising:
    installing a water testing apparatus within the water reservoir;
    passing water from the reservoir into an interior chamber of the water testing apparatus in response to increased water level in the water reservoir to provide a charge of water within the interior chamber;
    passing water through at least one contaminant indicator for detecting the presence of at least one contaminant in water passed to the interior chamber;

measuring the flow of water passing through said at least one contaminant indicator;

discharging water from the interior chamber by siphoning water from the interior chamber when the fluctuating water level drops within the reservoir.

20. A method according to claim 19 and further comprising venting the interior chamber as water is passing into the interior chamber.

21. A method according to claim 19 and further comprising venting a siphon as water is passing into the interior chamber.

22. A method according to claim 19 and further comprising:

venting the interior chamber as water is passing into the interior chamber;

venting a siphon as water is passing into the interior chamber.

23. A method according to claim 19 wherein said measuring is accomplished by counting charges of water passed into the interior chamber of a predetermined depth therein.

* * * * *